United States Patent [19]

Nishimura et al.

[11] 4,256,908

[45] Mar. 17, 1981

[54] PROCESS FOR PREPARING DIESTERS OF MALONIC ACID

[75] Inventors: Kenji Nishimura; Shinichi Furusaki; Yasushi Shiomi; Kozo Fujii; Keigo Nishihira; Masayoshi Yamashita, all of Ube, Japan

[73] Assignee: Ube Industries, Ltd., Yamaguchi, Japan

[21] Appl. No.: 50,762

[22] Filed: Jun. 21, 1979

[30] Foreign Application Priority Data

Jul. 3, 1978 [JP] Japan .................................. 53-79802
Dec. 6, 1978 [JP] Japan ................................ 53-150018

[51] Int. Cl.$^3$ ...................... C07C 67/36; C07C 67/38; C07C 69/38
[52] U.S. Cl. ................................................... 560/204

[58] Field of Search .......................................... 560/204

[56] References Cited

U.S. PATENT DOCUMENTS 4,138,580  2/1979  Umemura et al. .................. 560/204

FOREIGN PATENT DOCUMENTS 2634540  12/1977  Fed. Rep. of Germany .

Primary Examiner—Vivian Garner
Attorney, Agent, or Firm—Frishauf, Holtz, Goodman & Woodward

[57] ABSTRACT

A process for preparing a diester of malonic acid which comprises reacting ketene and carbon monoxide with an ester of nitrous acid catalytically in the presence of metallic palladium or a salt thereof.

7 Claims, No Drawings

PROCESS FOR PREPARING DIESTERS OF MALONIC ACID

This invention relates to a process for preparing a diester of malonic acid which comprises reacting ketene and carbon monoxide with an ester of nitrous acid catalytically in the presence of metallic palladium or a salt thereof.

A diester of malonic acid is of value as a starting material for preparing malonic acid, barbituric acid, barbital, medical compounds, agricultural chemicals, etc.

Heretofore, the diester of malonic acid has been prepared by the reaction of monochloroacetic acid with sodium cyanide in the presence of an alkali hydroxide to obtain sodium cyanoacetate followed by hydrolysis and subsequent esterification thereof. This process appears unsatisfactory from the economical viewpoint because this process involves complicated procedures and produces a great amount of undesired waste liquid containing a negative CN ion.

Other proposals on the preparation of the diester of malonic acid comprising the reaction of an ester of halogenated acetic acid and carbon monoxide with an alcohol have been made as seen below.

For instance, Japanese Patent Provisional Publication (JPPP) 50-111,015(1975) discloses the reaction carried out in the presence of a metal carbonyl catalyst and a basic compound; JPPP 51-146,414(1976) discloses the reaction carried out in the presence of a cobalt-containing compound catalyst and an alcolate of an alkali or alkaline earth metal or an alcoholic alkaline hydroxide; and JPPP 52-100,417(1977) discloses the reaction carried out in the presence of a basic compound and rhodium catalyst and, if desired, an iodine-containing compound.

Moreover, JPPP 53-7,613(1978) discloses the reaction of methylene dihalide and carbon monoxide with an alcohol in the presence of a cobalt carbonyl catalyst.

These processes, however, have a lot of drawbacks for the industrial uses which are, for instance, the use of expensive esters of halogenated acetic acid, necessity of a large amount of an alkali for absorbing the halogen evolved during the reaction, and the use of such a disadvantageous catalyst as cobalt carbonyl being difficult to a recycled efficiently or as an expensive rhodium or iodine compound. Therefore, these processes have not been adopted for practical uses.

The present inventors have been studying for the purpose of inventing a process for preparing a diester of malonic acid which is of value in the practical uses and have accomplished this invention which comprises reacting ketene and carbon monoxide with an ester of nitrous acid catalytically in the presence of metallic palladium or a salt thereof. The present catalytic reaction can be carried out in either the gaseous or liquid phase.

The present reaction is a novel one and seems to proceed in the following manner:

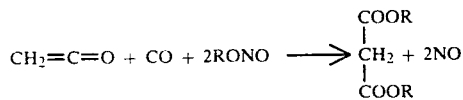

In the above equation, R represents an alkyl or cycloalkyl group.

The catalyst employed in this invention is metallic palladium or a salt thereof. The salt of palladium includes any of such salts that can be converted into the metallic palladium under the reaction conditions. Examples of said salt include nitrate, sulfate, phosphate, halide, and organic acid salts such as acetate, oxalate and benzoate. These examples also include palladium complex salts. The palladium employed in this invention is not necessary to be pure or alone, and any mixture of noble metals consisting mainly of palladium can be also employed.

The palladium and a salt thereof are preferably employed as being supported on an inactive carrier such as active carbon, alumina, silica, diatomaceous earth, pumice, zeolite, magnesium oxide, titanium oxide and molecular sieve. When the palladium or a salt thereof is employed with the carrier, the amount of palladium ranges from 0.1 to 20% by weight, ordinarily from 0.5 to 5% by weight, based on the amount of the carrier. When the salt is employed, the amount of the salt is calculated based on the above-mentioned ratio.

The ester of nitrous acid is selected from esters of nitrous acid with saturated monovalent aliphatic or alicyclic alcohols having 1-8 carbon atoms. Examples of said alcohols include aliphatic alcohols such as methanol, ethanol, n-propanol or isopropanol, n-butanol, isobutanol, sec-butanol or tert-butanol, n-amylalcohol or isoamylalcohol, hexanol, heptanol and octanol, and alicyclic alcohols such as cyclohexanol and methylcyclohexanol. These alcohols may contain substituents not disturbing the reaction, and examples of the substituents of these kinds include an alkoxy group etc.

The ester of nitrous acid may be fed into the reaction system in the form of other than the nitrous acid ester, that is, other substances that form the nitrous acid esters under the reaction conditions can be employed. For instance, an alcohol and a nitrogen oxide selected from nitrogen monoxide, nitrogen dioxide, dinitrogen trioxide and dinitrogen tetraoxide, or its hydrate can be charged into the reaction system, instead of using the nitrous acid ester, with optional employment of molecular oxygen-containing gas. Preferred examples of the hydrate of nitrogen oxide include nitric acid and nitrous acid. In these cases, the alcohol employed corresponds to the alcohol portion of the desired nitrous acid ester.

When the present invention is carried out in the gaseous phase, carbon monoxide, the ester of nitrous acid and ketene, all in the gaseous state, are introduced as such or together with a gaseous diluent onto the palladium catalyst to carry out the reaction.

In the gaseous phase reaction, the amounts of the reactants to be charged vary broadly regardless of the stoichiometric ratio based on the aforementioned reaction equation (1:1:2, molar ratio of ketene, carbon monoxide and ester of nitrous acid). For instance, the amount of the ester of nitrous acid preferably ranges from 1 to 20 moles, more preferably from 2 to 10 moles, per one mole of the ketene. The concentration of the mixture of the ketene and the ester of nitrous acid ranges from 1 to 20% in volume, preferably from 2 to 15% in volume, per the whole volume of the gas employed. The concentration of the carbon monoxide preferably is 1 or more % in volume per the whole volume of the gas employed.

The gaseous phase reaction can proceed at a temperature of not less than 40° C. and under ordinary pressure, but is preferably carried out at a temperature ranging from 80° to 150° C. The reaction may be carried out under elevated or reduced pressure. Practically, the present process can be carried out in the vessel on either a fixed or fluid bed. The time of period for the contact of the introduced gases with the solid catalyst is preferably not more than 10 seconds, more preferably between 0.2 and 5 seconds.

When the present reaction is carried out in the liquid phase, the ketene, ester of nitrous acid and carbon monoxide are supplied into a suspension of the palladium catalyst in an organic solvent to carry out the reaction. Examples of said organic solvent include optionally halogenated aliphatic hydrocarbons such as pentane, hexane, cyclohexane, chloroform, trichloroethylene and perchloroethylene, optionally halogenated aromatic hydrocarbons such as benzene, toluene, xylene, decalin, tetralin, chlorobenzene and dichlorobenzene, esters such as an oxalic acid ester, an acetic acid ester and a carbonic acid ester, ethers such as dioxane and diethyl ether, and ketones such as acetone and methyl ethyl ketone.

In the liquid phase reaction, the amount of ketene employed is preferably not more than 10 mole/g(Pd)·hr. The amount of the nitrous acid ester is preferably not less than the stoichiometric ratio, namely, not less than 2 moles per 1 mole of the ketene.

The liquid phase reaction is preferably carried out at a temperature from room temperature to 200° C. and under the partial carbon monoxide pressure of not less than 0.5 Kg/cm$^2$·G.

This invention will be further described by the following non-limiting examples. In Examples 1 through 10, the reaction tube was one made of hard glass (inner diameter: 25 mm, height: 400 mm). In Examples 11 through 27, the autoclave was a stainless steel-made autoclave with a magnetic stirrer (inner volume: 200 ml).

EXAMPLE 1

Into a reaction tube charged with 10 ml of an alumina catalyst pellet carrying 0.5% by weight of metallic palladium thereon (available from Japan Engelhard Co., Ltd.) was introduced a gaseous mixture of carbon monoxide, ketene, ethyl nitrite and nitrogen (40:1.4:8.5:50, volume ratio, respectively) at a rate of 48 liters per hour, and the reaction was carried out at 115° C. and under ordinary pressure.

Gas chromatographic analysis of the resulting product revealed diethyl malonate produced at a rate of 135 g/l·(catalyst)·hr. and by-produced diethyl oxalate.

EXAMPLE 2

The procedures of Example 1 were repeated except that the gaseous mixture was replaced with a mixture of carbon monoxide, ketene, ethyl nitrite and nitrogen (55:1.0:3.5:40.5, volume ratio, respectively).

Gas chromatographic analysis of the resulting product revealed diethyl malonate produced at a rate of 94 g/l·(catalyst)·hr. and by-produced diethyl oxalate.

EXAMPLE 3

Into a reaction tube charged with 20 ml of a spheric silicon carbide catalyst (diameter: 4 mm) carrying 1% by weight of metallic palladium thereon was introduced a gaseous mixture of carbon monoxide, ketene, ethyl nitrite and nitrogen (49.5:2.0:9.4:39.1, volume ratio, respectively) at a rate of 40.2 liters per hour, and the reaction was carried out at 115° C. and under ordinary pressure.

Gas chromatographic analysis of the resulting product revealed diethyl malonate produced at a rate of 68 g/l·(catalyst)·hr. and by-produced diethyl oxalate.

EXAMPLE 4

Into a reaction tube charged with 10 ml of the catalyst as described in Example 1 was introduced a gaseous mixture of carbon monoxide, ketene, methyl nitrite and nitrogen (60:1.3:8.0:30.7, volume ratio, respectively) at a rate of 37.8 liters per hour, and the reaction was carried out at 140° C. and under ordinary pressure.

Gas chromatographic analysis of the resulting product revealed dimethyl malonate produced at a rate of 110 g/l·(catalyst)·hr. and by-produced dimethyl oxalate.

EXAMPLE 5

Into a reaction tube charged with 10 ml of the catalyst as described in Example 1 was introduced and a gaseous mixture of carbon monoxide, ketene, ethyl nitrite and nitrogen (20:0.2:8.5:71.3, volume ratio, respectively) at a rate of 48 liters per hour, and the reaction was carried out at 120° C. and under ordinary pressure.

Gas chromatographic analysis of the resulting product revealed diethyl malonate produced at a rate of 50 g/l·(catalyst)·hr. and by-produced diethyl oxalate.

EXAMPLE 6

Into a reaction tube charged with 10 ml of the catalyst as described in Example 1 was introduced a gaseous mixture of carbon monoxide, ketene, ethyl nitrite and nitrogen (9:0.7:7.5:82.8, volume ratio, respectively) at a rate of 41 liters per hour, and the reaction was carried out at 115° C. and under ordinary pressure.

Gas chromatographic analysis of the resulting product revealed diethyl malonate produced at a rate of 81 g/l·(catalyst)·hr. and by-produced diethyl oxalate.

EXAMPLE 7

Into a reaction tube charged with 10 ml of a spheric titanium dioxide catalyst carrying 0.5% by weight of metallic palladium thereon was introduced a gaseous mixture of carbon monoxide, ketene, ethyl nitrite and nitrogen (30:0.3:8:61.7, volume ratio, respectively) at a rate of 45 liters per hour, and the reaction was carried out at 120° C. and under ordinary pressure.

Gas chromatographic analysis of the resulting product revealed diethyl malonate produced at a rate of 60 g/l·(catalyst)·hr. and by-produced diethyl oxalate.

EXAMPLE 8

A reaction tube charged with 10 ml of a spheric active carbon catalyst carrying 0.2 g of palladium nitrate thereon was prepared, and then the procedures of Example 3 were repeated.

Gas chromatographic analysis of the resulting product revealed diethyl malonate produced at a rate of 50 g/l·(catalyst)·hr. and by-produced diethyl oxalate.

EXAMPLE 9

A reaction tube charged with 10 ml of a spheric active carbon catalyst carrying 0.2 g of palladium chloride thereon was prepared, and then the procedures of Example 3 were repeated.

Gas chromatographic analysis of the resulting product revealed diethyl malonate produced at a rate of 25 g/l·(catalyst)·hr. and by-produced diethyl oxalate.

EXAMPLE 10

A reaction tube charged with 10 ml of a spheric active carbon catalyst carrying 0.2 g of palladium acetate thereon was prepared, and then the procedures of Example 3 were repeated.

Gas chromatographic analysis of the resulting product revealed diethyl malonate produced at a rate of 35 g/l·(catalyst)·hr. and by-produced diethyl oxalate.

EXAMPLE 11

Using the same reaction tube and catalyst as in Example 1, a gaseous mixture consisting of carbon monoxide, ketene, n-hexyl nitrite and nitrogen (55:0.8:6.7:37.5, volume ratio) was introduced into the reaction tube at a rate of 39.6 l./hr. and the reaction was conducted at a temperature of 120° C. under ordinary pressure. After reaction, the reaction product was analyzed by gas chromatography. As the result, it was found that di-n-hexyl malonate was produced at a rate of 24 g/l·(catalyst)·hr. and di-n-hexyl oxalate was produced as a by-product.

EXAMPLE 12

An autoclave charged with 100 ml of a diethyl oxalate suspension in which 2 g of active carbon catalyst carrying 5% by weight of metallic palladium thereon was suspended was purged with carbon monoxide. The content was then heated to 100° C. under stirring, and carbon monoxide was pressed into the autoclave until the inner pressure reached 10 kg/cm$^2$·G.

Into the autoclave were pressed a ketene-containing carbon monoxide prepared by bubbling carbon monoxide through liquid ketene and ethyl nitrite, and the reaction was carried out over 3 hours. During the reaction, 268 millimoles of ketene and 1,584 millimoles of ethyl nitrite were supplied, maintaining the inner pressure at 10 kg/cm$^2$·G. by controlling the rate of exhaust gas. The resulting reaction liquid was analyzed with gas chromatography.

EXAMPLE 13

The precedures of Example 12 were repeated except that the charged suspension was replaced with 0.17 g of palladium chloride suspended in 100 ml. of dioxane and that the reaction was carried out over 2 hours with supply of 194 millimoles of ketene and 1,080 millimoles of ethyl nitrite.

EXAMPLE 14

An autoclave charged with 100 ml. of di-n-butyl oxalate suspension in which 2 g of active carbon catalyst carrying 5% by weight of metalic palladium thereon was suspended was purged with carbon monoxide. The content was then heated to 100° C. under stirring, and carbon monoxide was pressed into the autoclave until the inner pressure reached 10 atmospheric pressure.

Into the autoclave were pressed a ketene-containing carbon monoxide prepared by bubbling carbon monoxide through liquid ketene and n-butyl nitrite, and the reaction was carried out over 2 hours. During the reaction, 201 millimoles of ketene and 774 millimoles of n-butyl nitrite were supplied, maintaining the inner pressure at 10 kg/cm$^2$·G. by controlling the rate of exhaust gas. The resulting reaction liquid was analyzed with gas chromatography.

EXAMPLES 15-28

The procedures of Example 13 were repeated except that the catalyst, solvent, reaction conditions and amount of supply of ketene and n-butyl nitrite were replaced as set out in the following table.

The results obtained in Examples 12-28 are also shown in the following table.

TABLE

| Ex. No. | Catalyst (g) | | Solvent | Reaction conditions pressure (kg/cm$^2$·G) | Reaction conditions temperature (°C.) | Supply (millimole) ketene | Supply (millimole) Nitrous acid ester | | Resulting malonic acid diester (millimole) |
|---|---|---|---|---|---|---|---|---|---|
| 12 | 5wt% Pd . C | 2 | Diethyl oxalate | 10 | 100 | 268 | | 1,584 | 38 |
| 13 | PdCl$_2$ | 0.17 | Dioxane | " | " | 194 | I | 1,080 | III 33 |
| 14 | 5wt% Pd . C | 2 | Di-n-butyl oxalate | " | " | 201 | | 774 | 35 |
| 15 | " | " | " | " | " | 235 | | 387 | 31 |
| 16 | " | " | " | " | " | 332 | | 774 | 40 |
| 17 | " | " | " | " | 80 | 210 | | " | 30 |
| 18 | " | " | " | " | 120 | " | | " | 48 |
| 19 | " | " | " | " | 140 | 226 | | " | 45 |
| 19 | " | " | " | " | 140 | 226 | | " | 45 |
| 20 | " | " | " | 1 | 100 | 175 | | " | 16 |
| 21 | " | " | Dioxane | 10 | " | 184 | II | " | IV 20 |
| 22 | " | " | Toluene | " | " | 203 | | " | 28 |
| 23 | " | " | Chlorobenzene | " | " | 184 | | " | 30 |
| 24 | " | " | Cyclohexane | " | " | 190 | | " | 26 |
| 25 | Pd(NO$_3$)$_2$ | 0.2 | Di-n-butyl oxalate | " | " | 117 | | " | 16 |
| 26 | (8wt% Pd + 2wt% Pt) . C | 0.78 | " | " | " | 212 | | " | 31 |
| 27 | PdCl$_2$ | 0.17 | " | " | " | 203 | | " | 72 |
| 28 | " | " | Dioxane | " | " | 166 | | " | 62 |

Note
I: Ethyl nitrite.
II: n-Butyl nitrite.
III: Diethyl malonate.
IV: Di-n-butyl malonate

We claim:

1. A process for preparing a diester of malonic acid which comprises reacting ketene and carbon monoxide with an ester of nitrous acid catalytically in the presence of metallic palladium or a salt thereof in (i) a gaseous phase at a temperature ranging from 80° to 150° C. or (ii) in a liquid phase at a temperature ranging from room temperature to 200° C., said ester being selected from esters of nitrous acid with saturated monovalent aliphatic or alicyclic alcohols having 1–8 carbon atoms.

2. A process as claimed in claim 1, wherein the reaction is carried out by the contact of the gaseous reactants with the metallic palladium or salt thereof on a fixed or fluid bed over a period of time ranging from 0.2 to 5 seconds.

3. A process as claimed in claim 1, wherein the reaction is carried out in a suspension of the metallic palladium or salt thereof in an organic solvent.

4. A process as claimed in claim 3, wherein said organic solvent is selected from the group consisting of aliphatic hydrocarbons, halogenated aliphatic hydrocarbons, aromatic hydrocarbons, halogenated aromatic hydrocarbons, esters, and ketones.

5. A process as claimed in claim 1, wherein the reaction is carried out under a partial carbon monoxide pressure of not less than 0.5 kg/cm$^2$·G.

6. A process as claimed in claim 1, wherein the salt of palladium is a nitrate, sulfate, phosphate, halide, acetate, oxalate or benzoate.

7. A process as claimed in claim 1, wherein the palladium or salt thereof is supported on an inactive carrier.

* * * * *

UNITED STATES PATENT AND TRADEMARK OFFICE
CERTIFICATE OF CORRECTION

PATENT NO. : 4,256,908
DATED : March 17, 1981
INVENTOR(S) : Kenji NISHIMURA et al It is certified that error appears in the above-identified patent and that said Letters Patent are hereby corrected as shown below:

Column 6, line 13: change "metalic" to --metallic--.

Column 6, under the Table, delete one occurrence of Example 19 and the data therefor.

Signed and Sealed this

Twenty-ninth Day of December 1981

[SEAL]

Attest:

GERALD J. MOSSINGHOFF

Attesting Officer    Commissioner of Patents and Trademarks